(12) United States Patent
Borden (10) Patent No.: US 8,728,320 B2
(45) Date of Patent: May 20, 2014

(54) LIGNIN SORBENT, LIGNIN REMOVAL UNIT, BIOREFINERY, PROCESS FOR REMOVING LIGNIN, PROCESS FOR BINDING LIGNIN AND RENEWABLE MATERIAL

(75) Inventor: Jacob Borden, Chicago, IL (US)

(73) Assignee: BP Corporation North America Inc., Houston, TX (US)

( * ) Notice: Subject to any disclaimer, the term of this patent is extended or adjusted under 35 U.S.C. 154(b) by 795 days.

(21) Appl. No.: 12/491,809

(22) Filed: Jun. 25, 2009

(65) Prior Publication Data

US 2010/0331560 A1    Dec. 30, 2010

(51) Int. Cl.
| | | |
|---|---|---|
| *B01D 15/00* | (2006.01) | |
| *B01J 20/22* | (2006.01) | |
| *B01J 20/24* | (2006.01) | |
| *C07C 31/08* | (2006.01) | |
| *C07C 57/00* | (2006.01) | |
| *C12P 1/00* | (2006.01) | |

(52) U.S. Cl.
USPC ............ 210/638; 44/307; 44/605; 127/1; 127/34; 127/36; 502/403; 502/514; 502/515; 210/263; 210/269; 210/511; 210/663; 210/669; 210/670; 210/773; 210/774; 435/72; 435/134; 435/165; 435/283.1; 435/294.1; 435/297.1

(58) Field of Classification Search
USPC ........ 210/182, 202, 209, 259, 511, 632, 634, 210/638, 639, 663, 669, 670, 674, 773, 774, 210/749, 766, 806, 263, 266, 269, 284, 210/502.1, 660, 679; 127/1, 2, 9, 32, 36, 127/37, 34; 162/21, 261; 435/72, 161, 163, 435/165, 134, 283.1, 297.1, 294.1; 44/302, 44/307, 605, 606; 502/1, 20, 400–404, 502/514, 515
See application file for complete search history.

(56) References Cited

U.S. PATENT DOCUMENTS

| | | | | |
|---|---|---|---|---|
| 3,998,732 | A * | 12/1976 | Solbach et al. | 210/670 |
| 4,902,425 | A * | 2/1990 | Keeney | 210/634 |
| 4,938,874 | A * | 7/1990 | Auchincloss | 210/662 |
| 5,089,134 | A * | 2/1992 | Ando et al. | 210/496 |
| 5,705,369 | A * | 1/1998 | Torget et al. | 435/105 |
| 6,190,503 | B1 | 2/2001 | Linhart et al. | |
| 6,322,701 | B1 * | 11/2001 | Delighiannis | 210/620 |
| 6,409,841 | B1 * | 6/2002 | Lombard | 127/37 |

(Continued)

FOREIGN PATENT DOCUMENTS

| | | |
|---|---|---|
| WO | WO02/37981 A2 | 5/2002 |
| WO | WO 2009/120931 A2 | 10/2009 |

OTHER PUBLICATIONS

Cai et al., "Poly(N-ethylacrylamide) Hydrogels for Lignin Separation", Ind. Eng. Chem. Res. 2001 pp. 3406-3412.

(Continued)

Primary Examiner — Joseph Drodge
(74) Attorney, Agent, or Firm — John P. Poliak (57) ABSTRACT

This invention relates to a lignin sorbent, a lignin removal unit, a biorefinery, a process for removing lignin, a process for binding lignin, and a renewable material. The lignin sorbent includes a substrate, and a lignin binding material dispersed with respect to the substrate. The lignin binding process includes the step of adding a lignin binding material to an input stream, and the step of converting the input stream into a renewable material.

15 Claims, 8 Drawing Sheets

(56) References Cited

U.S. PATENT DOCUMENTS

| | | | |
|---|---|---|---|
| 7,029,202 B2* | 4/2006 | Zhuang | 405/128.5 |
| 7,311,832 B2* | 12/2007 | Demmer et al. | 210/502.1 |
| 7,604,967 B2 | 10/2009 | Yang et al. | |
| 7,666,637 B2* | 2/2010 | Nguyen | 435/165 |
| 7,875,444 B2 | 1/2011 | Yang et al. | |
| 8,012,356 B2* | 9/2011 | Funaoka et al. | 210/691 |
| 8,415,122 B2* | 4/2013 | Medoff et al. | 435/161 |
| 8,496,984 B2* | 7/2013 | Tranquil et al. | 426/321 |
| 2004/0231060 A1 | 11/2004 | Burdette et al. | |
| 2006/0251764 A1 | 11/2006 | Abbas et al. | |
| 2007/0128334 A1 | 6/2007 | Pittman | |
| 2007/0298477 A1 | 12/2007 | Kratochvil et al. | |
| 2008/0044877 A1* | 2/2008 | Penttila et al. | 435/165 |
| 2008/0128358 A1* | 6/2008 | Nussbaumer et al. | 210/658 |
| 2009/0118477 A1* | 5/2009 | Hallberg et al. | 530/500 |
| 2010/0028484 A1* | 2/2010 | Kriesler et al. | 426/7 |
| 2010/0159515 A1* | 6/2010 | Cirakovic | 435/72 |
| 2010/0189706 A1* | 7/2010 | Chang et al. | 424/94.4 |
| 2010/0263814 A1* | 10/2010 | Dottori et al. | 162/21 |
| 2010/0269990 A1* | 10/2010 | Dottori et al. | 162/21 |
| 2010/0287826 A1* | 11/2010 | Hoffman et al. | 44/605 |

OTHER PUBLICATIONS

A. Aden, M. Ruth, K. Ibsen, J. Jechura, K. Neeves, J. Sheehan and B. Wallace, Lignocellulosic Biomass to Ethanol Process Design and Economics Utilizing Co-Current Dilute Acid Prehydrolysis and Enzymatic Hydrolysis for Corn Stover, National Renewable Energy Laboratory, Technical Report, Jun. 2002 (154 pgs).

A. Berlin, M. Balakshin, N. Gilkes, J. Kadla, V. Maximenko, S. Kubo and. J. Saddler, Inhibation of cellulas, xylanase and β-glucosidas activities by softwood lignin preparation, Science Direct, Journal of Biotechnology, 2006 (12 pgs).

M. Himmel, S. Ding, D. Johnson, W. Adney, M. Nimlos, J. Brady and T. Foust, Biomass Recalcitrance: Engineering Plants and Enzymes for Biofuels Production, Science, vol. 315, Feb. 9, 2007 (4 pgs.).

M. Sticken, Plant genetic engineering to improve biomass characteristics for biofuels, Science Direct, 2006 (5 pgs).

* cited by examiner

LIGNIN SORBENT, LIGNIN REMOVAL UNIT, BIOREFINERY, PROCESS FOR REMOVING LIGNIN, PROCESS FOR BINDING LIGNIN AND RENEWABLE MATERIAL

BACKGROUND

1. Technical Field

This invention relates to a lignin sorbent, a lignin removal unit, a lignocellulosic biorefinery, a process for removing lignin, a process for binding lignin, and a renewable material.

2. Discussion of Related Art

Tightening oil supplies and escalating energy prices along with environmental concerns over nonrenewable resources have prompted significant interest and research into renewable materials and/or biofuels. Efforts to reduce carbon emissions and greenhouse gases are also driving investment into renewable materials and/or biofuels.

One area of cost for production of renewable materials is hydrolytic enzymes. Stephanopoulos, Challenges in Engineering Microbes for Biofuels Production, states "[d]espite substantial reduction in the cost of cellulolytic enzymes [ ], sugar release from biomass still remains an expensive and slow step, perhaps the most critical in the overall process."

Himmel et al, Biomass Recalcitrance: Engineering Plants and Enzymes for Biofuels Production, states the "cost-competitive production of biofuels is currently prevented by the high cost of biomass feedstocks and the processes for converting biomass to sugars—that is, the cost of the thermochemical pretreatment and enzyme hydrolysis unit operations in a biorefinery."

Sticklen, Plant genetic engineering to improve biomass characteristics for biofuels, states the "idea that fermentable sugars for use in the production of alcohol fuels could be derived from crop biomass has been well received by the US Federal government; however, major economical downsides of biomass refineries include the pretreatment processing of the lignocellulosic matter and the cost of production of the microbial cellulases needed to convert the cellulose of biomass into fermentable sugars."

Aden et al., Lignocellulosic Biomass to Ethanol Process Design and Economics Utilizing Co-current Dilute Acid Prehydrolysis and Enzymatic Hydrolysis for Corn Stover, published by the National Renewable Energy Laboratory discloses an ethanol plant process design using corn stover for a feedstock. The entire teachings of Aden et al. are hereby incorporated by reference in their entirety.

However, even with the above improvements in the processes, there is a need and a desire to reduce usage enzyme costs and produce renewable materials in a more cost effective manner.

SUMMARY

This invention relates to a lignin sorbent, a lignin removal unit, a lignocellulosic biorefinery, a process for removing lignin, a process for binding lignin, and a renewable material. This invention may reduce usage enzyme costs and produce renewable materials in a more cost effective manner. Hydrolytic enzymes act as a catalyst and are not consumed in reactions to depolymerize lignocellulosic material, but lignin present in feedstock materials can consume the hydrolytic enzymes. Methods to remove and/or preferentially bind lignin can reduce enzyme operating costs and production costs of the renewable material.

According to a first embodiment, the invention includes a lignin sorbent suitable for use in production of renewable materials. The sorbent includes a substrate, and a lignin binding material dispersed with respect to the substrate.

According to a second embodiment, the invention includes a lignin removal unit suitable for use in production of renewable materials. The unit includes a feed line for receiving a feed stream comprising soluble lignin or insoluble lignin, and at least one lignin removal device having a lignin sorbent for sorbing the lignin with the at least one lignin removal device is in fluid communication with the feed line. The unit includes a regeneration line for supplying a release material to the at least one lignin removal device with the regeneration line in fluid communication with the at least one lignin removal device. The unit includes a lignin line for removing the lignin from the at least one lignin removal device with the lignin line in fluid communication with the lignin removal device.

According to a third embodiment, the invention includes a cellulosic biorefinery suitable for production of renewable materials. The biorefinery includes a pretreatment unit for depolymerization and/or solubilization of lignin, cellulose, hemicellulose and/or combinations thereof of a feedstock stream to a pretreated stream. The biorefinery includes a lignin removal unit before the pretreatment unit and/or after the pretreatment unit for removing lignin, and a hydrolysis unit for depolymerization of lignin, cellulose, hemicellulose, and/or combinations thereof to a renewable-based feedstock steam. The biorefinery includes a conversion unit for receiving the renewable-based feedstock stream and converting the renewable-based feedstock stream into a conversion unit effluent stream, and a separation unit for receiving the conversion unit effluent stream and forming a renewable material containing stream and a byproduct stream. The biorefinery includes a regeneration line to supply release material for release of the lignin from the lignin removal unit, and a lignin line from the lignin removal unit to flow the lignin.

According to a fourth embodiment, the invention includes removing lignin with a process suitable for production of renewable materials. The process includes the step of sorbing lignin on a lignin sorbent to separate lignin from a remainder of an input stream, and the step of releasing the lignin from the lignin sorbent.

According to a fifth embodiment, the invention includes binding lignin with a process suitable for production of renewable materials. The process includes the step of adding a lignin binding material to an input stream, and the step of converting the input stream into a renewable material.

According to a sixth embodiment, the invention includes a renewable material made by any of the sorbents, units, biorefineries, removing processes, and/or binding processes disclosed herein.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention. In the drawings.

DETAILED DESCRIPTION

This invention may include a lignin sorbent, a lignin removal unit, a lignocellulosic biorefinery, a process for removing lignin, a process for binding lignin, and/or a renewable material.

Cocktails of enzymes can hydrolyze and/or degrade cellulose to monomer sugar units. Cocktails of enzymes and/or hydrolysis techniques can include cellulases, hemicellulases, ligninases, lytic enzymes endocellulase, exocellulase, β-glucosidase, cellobiose dehydrogenase, manganese peroxidase, lignin peroxidase, and/or the like. The cost of cocktails of enzymes can be an economic driver for utilization of lignocellulosic material in fuels, chemicals, and/or the like.

Lignocellulosic biomass can be pretreated to disrupt the heteropolymer matrix of cellulose, hemicellulose, lignin, and/or the like. Solubilized lignin (pretreated) and/or residual solid-phase lignin can reversibly bind enzymes in the aqueous cocktail of enzymes. The result of lignin-enzyme interaction during hydrolysis can be a reduction in an effective enzyme concentration and/or effective hydrolysis rate of cellulose and hemicellulose to fermentable sugars.

According to one embodiment, the invention can include exogenously added solids having a high protein content, such as distillers dried grains with solubles (DDGS). The solids can be added as a fraction of a total solids fed into a pretreatment reactor and/or unit. An amount of high-protein solids can be tuned and/or adjusted based on lignin type, lignin content, lignin-enzyme interaction, and/or the like of the pretreated lignocellulose. The exogenously added solids (protein) can bind lignin prior to addition of lytic enzymes (cocktail of enzymes), such as to preclude and/or reduce inhibition of lytic enzymes by lignin.

In another embodiment, the exogenous protein can be immobilized on a solid support. Support-immobilized proteins could be added before, during, and/or after pretreatment for absorption of lignin prior to addition of lytic enzymes. After removal and/or filtering of pretreated solid lignocellulose, the support-immobilized proteins can be suspended in an appropriately buffered and/or pH-adjusted solution to disrupt lignin-enzyme interactions and/or complexes, such as to release a purified lignin suitable for further chemical modification, sales, combustion, and/or the like. Released support-immobilized proteins can be recycled and/or reused.

The ability to remove lignin prior to introduction of lytic enzymes can increase an effective enzyme activity and/or reduce an amount of enzymes needed for conversion of lignocellulose to fuels, chemicals, and/or the like.

Enzymes that hydrolyze biomass can be a significant expense in production of fuels, chemicals, and/or the like from lignocellulose. A significant portion of added lytic enzymes can be ineffective due to interaction with lignin exposed during pretreatment, as discussed above. According to one embodiment, the invention can include methods for preventing lignin inhibition of lytic enzymes.

In a first method, high-protein solids (exogenous protein) can be added with biomass prior to pretreatment. Before, during, and/or after pretreatment, lignin can interact with the exogenous protein rather than the lytic enzymes.

In a second method, solid-support-immobilized proteins can be added after pretreatment and/or prior to addition of the lytic enzymes. The solid-support-immobilized proteins can prevent interaction of lignin with lytic enzymes and allows for recovery of lignin and the solid support immobilized proteins. Both methods can allow and/or provide for a reduction in an amount of lytic enzymes needed for lignocellulose hydrolysis and conversion to fuels, chemicals, and/or the like.

Figure 1:
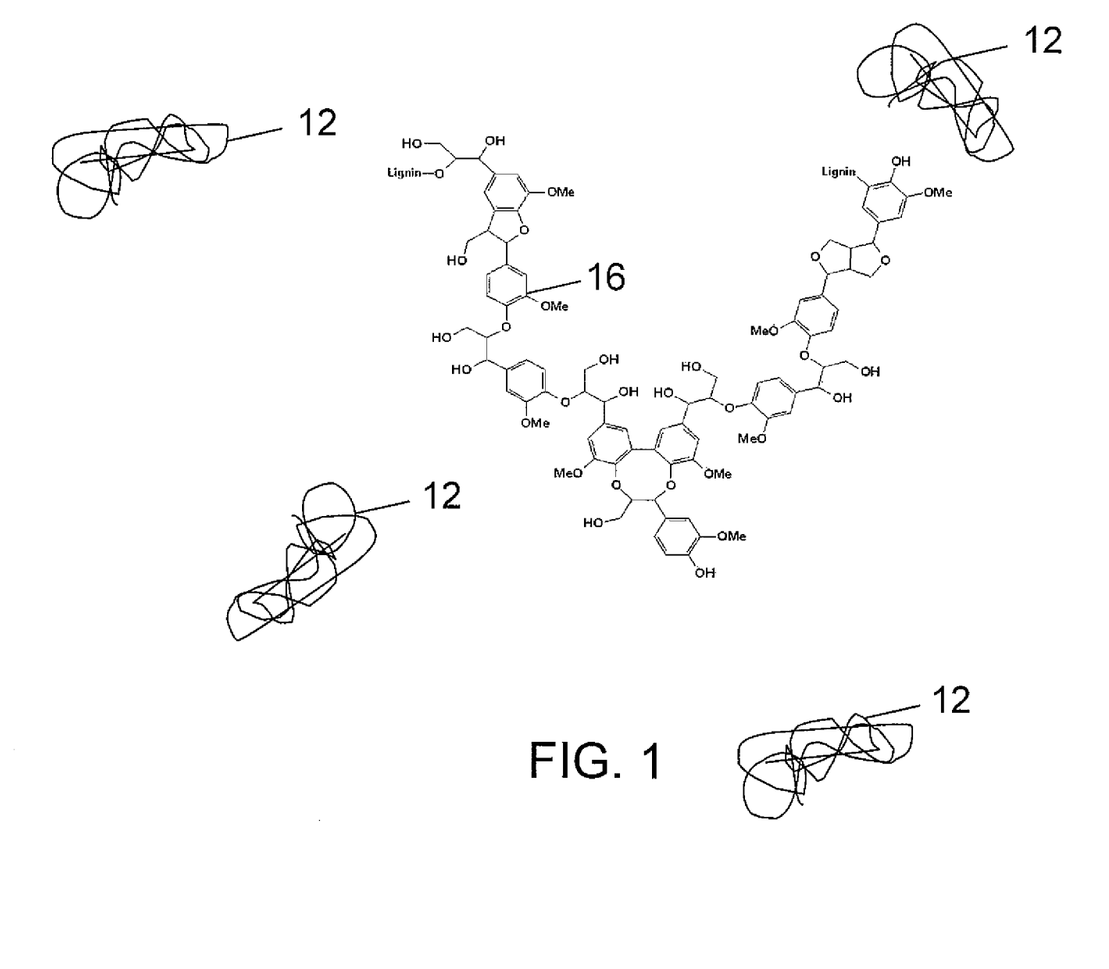
FIG. 1 illustrates a lignin binding material, according to one embodiment.

FIG. 1 illustrates a lignin binding material 12 in solution with lignin 16, according to one embodiment.

Figure 2:
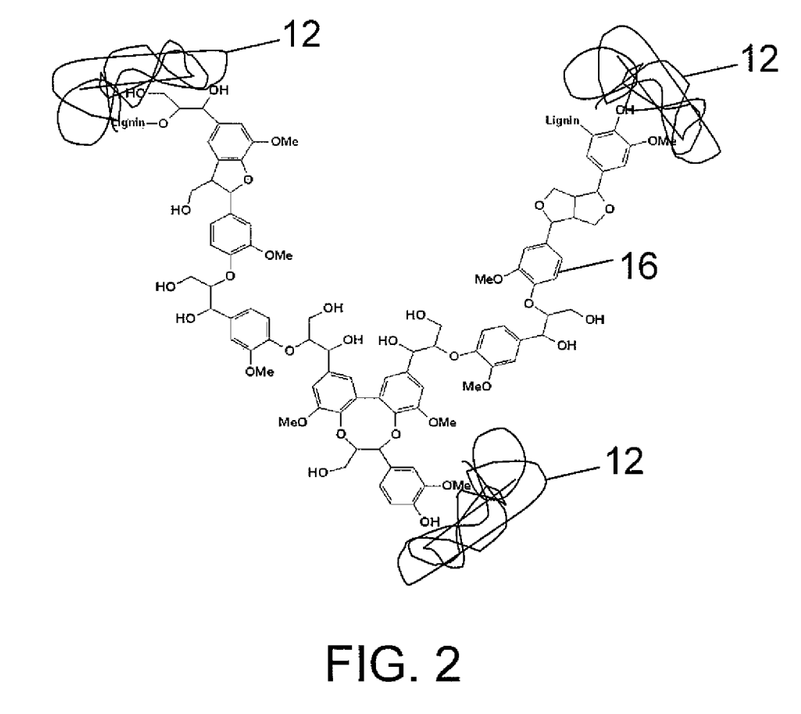
FIG. 2 illustrates a lignin binding material, according to one embodiment.

FIG. 2 illustrates a lignin binding material 12 bound to lignin 16, according to one embodiment.

Figure 3:
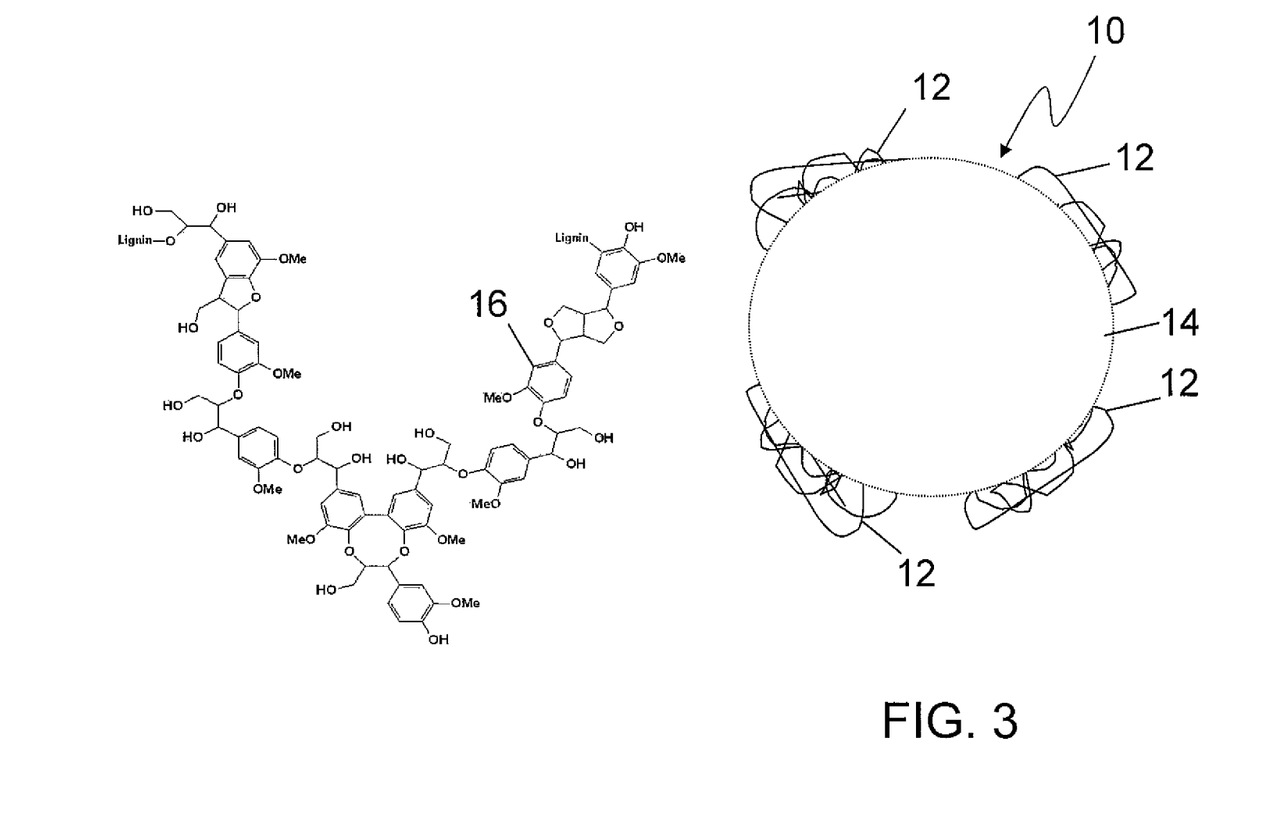
FIG. 3 illustrates a lignin sorbent, according to one embodiment.

FIG. 3 illustrates a lignin sorbent 10, according to one embodiment. The lignin sorbent 10 includes a lignin binding material 12 dispersed and/or disposed with respect to a substrate 14, such as for sorbing lignin 16.

Figure 4:
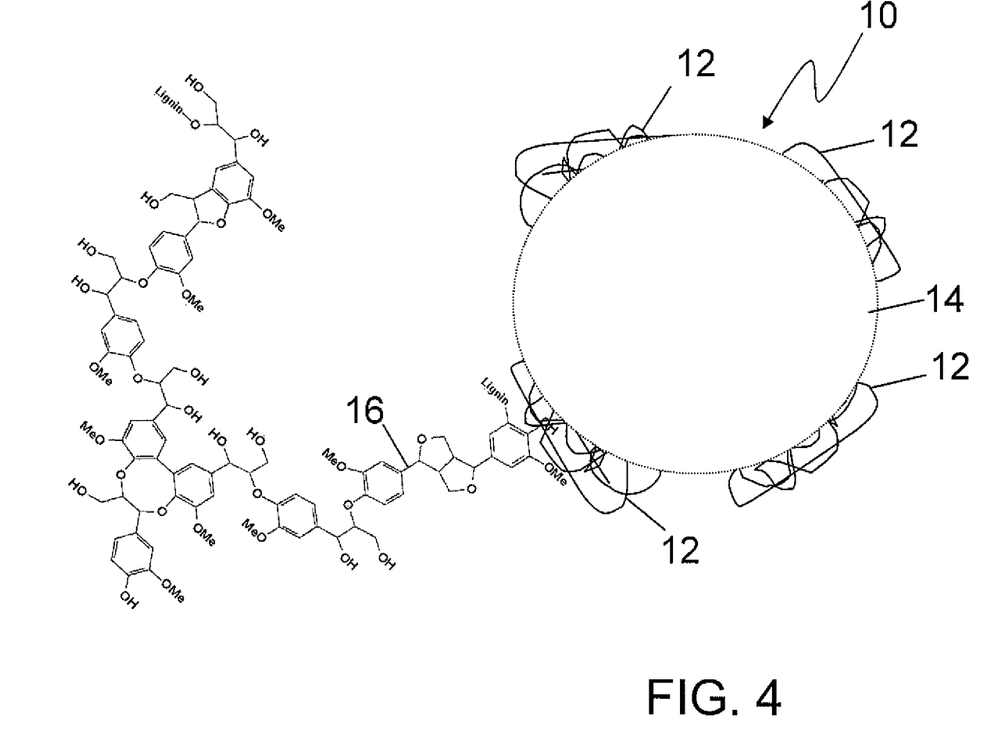
FIG. 4 illustrates a lignin sorbent, according to one embodiment.

FIG. 4 illustrates a lignin sorbent 10, according to one embodiment. The lignin sorbent 10 includes a lignin binding material 12 dispersed and/or disposed with respect to a substrate 14. The lignin sorbent 10 has a bound piece of lignin 16.

Figure 5:
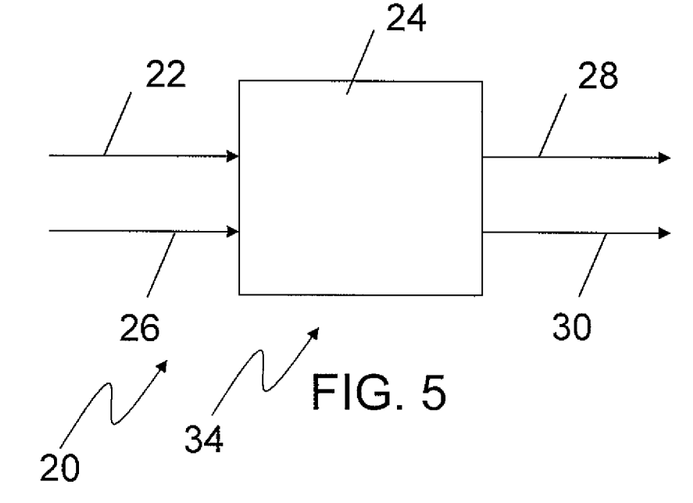
FIG. 5 illustrates a lignin removal unit, according to one embodiment.

FIG. 5 illustrates a lignin removal unit 20, according to one embodiment. The lignin removal unit 20 includes a feed line 22 connected to a lignin removal device 24. The lignin removal unit 20 includes a regeneration line 26, a lignin line 28, and a product line 30 each connected to it. The lignin removal device 24 includes an internal heat mechanism 34, such as direct hot water injection, an internal electric heater, an internal steam coil, a heat jacket, and/or the like.

Figure 6:
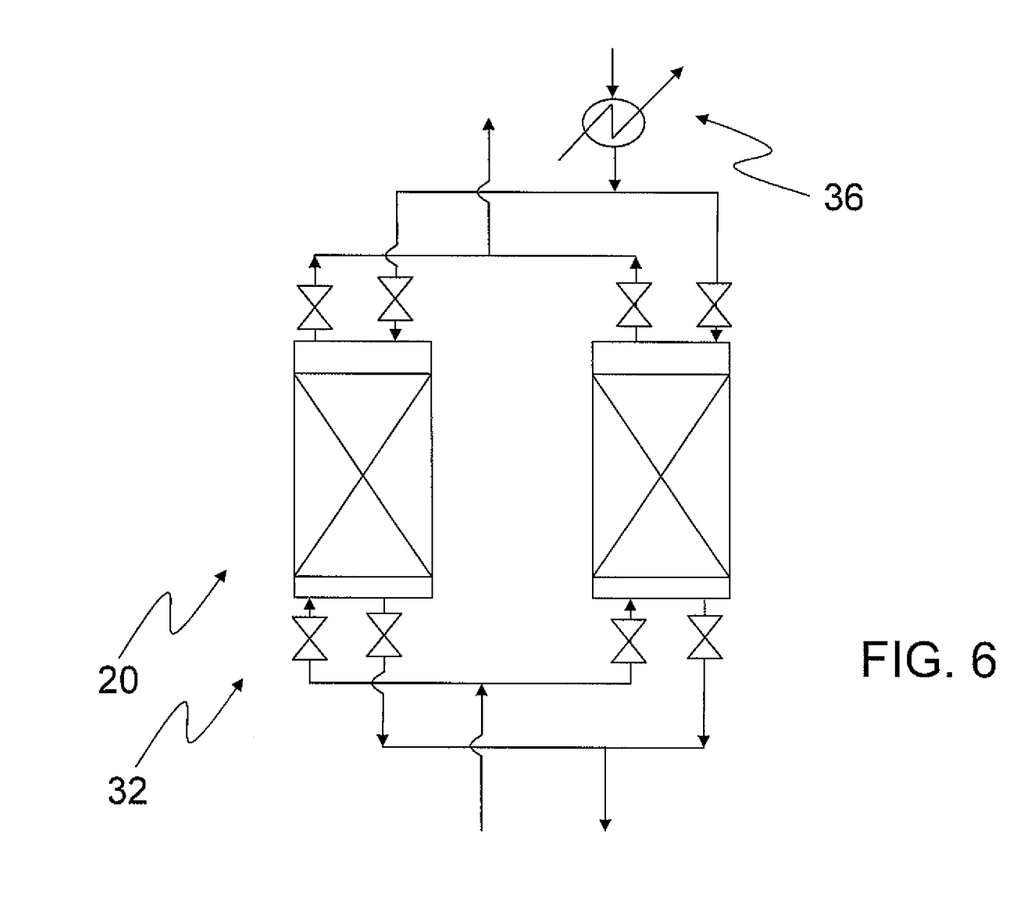
FIG. 6 illustrates a lignin removal unit, according to one embodiment.

FIG. 6 illustrates a lignin removal unit 20, according to one embodiment. The lignin removal unit 20 includes packed beds 32 and an external heat mechanism 36, such as a heat exchanger for thermal transfer of a regeneration material with a suitable fluid. Heat exchangers can include shell and tube exchangers, plate and frame exchangers, helical heat exchangers, extended surface area heat exchangers, and/or the like.

Figure 7:
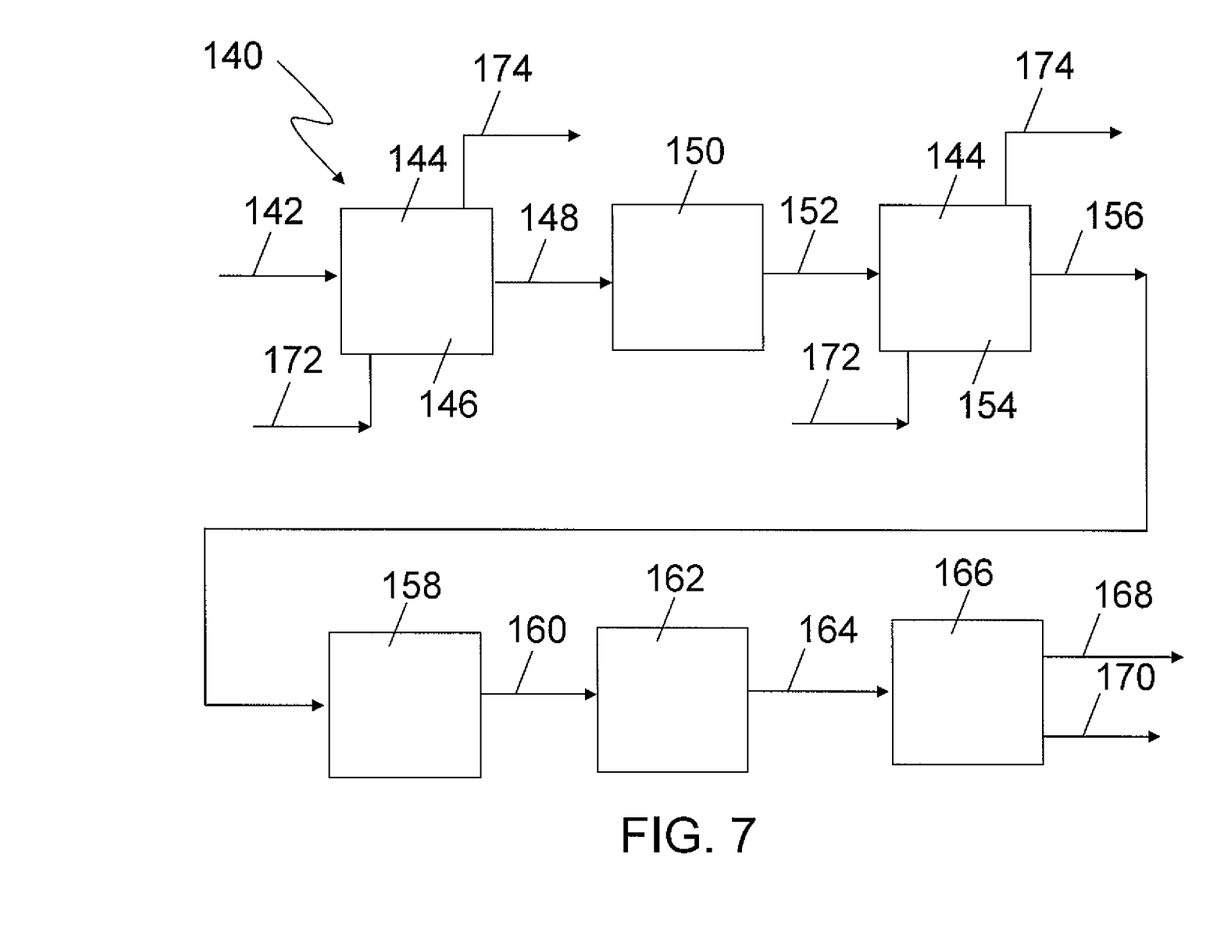
FIG. 7 illustrates a biorefinery illustrates a biorefinery, according to one embodiment.

FIG. 7 illustrates a cellulosic biorefinery 140, according to one embodiment. The cellulosic biorefinery 140 includes a feedstock stream 142 connected to a lignin removal unit 144, such as a feedstock lignin removal unit 146 to form a pretreatment influent stream 148. The pretreatment influent stream 148 connects to a pretreatment unit 150 to form a pretreated stream 152. Optionally, the pretreated stream 152 connects to a lignin removal unit 144, such as a pretreated lignin removal unit 154 to form a hydrolysis influent stream 156. The hydrolysis influent stream 156 connects to a hydrolysis unit 158 to form a renewable-based feedstock stream 160. The renewable-based feedstock stream 160 connects to a conversion unit 162 to form a conversion unit effluent stream 164. The conversion unit effluent stream 164 connects to a separation unit 166 to form a product stream 168 and a byproduct stream 170. Each lignin removal unit 144 connects with a regeneration line 172 and a lignin line 174. Embodiments of a biorefinery with one or more lignin removal units at a suitable location in the process are within the scope of this invention.

Figure 8:
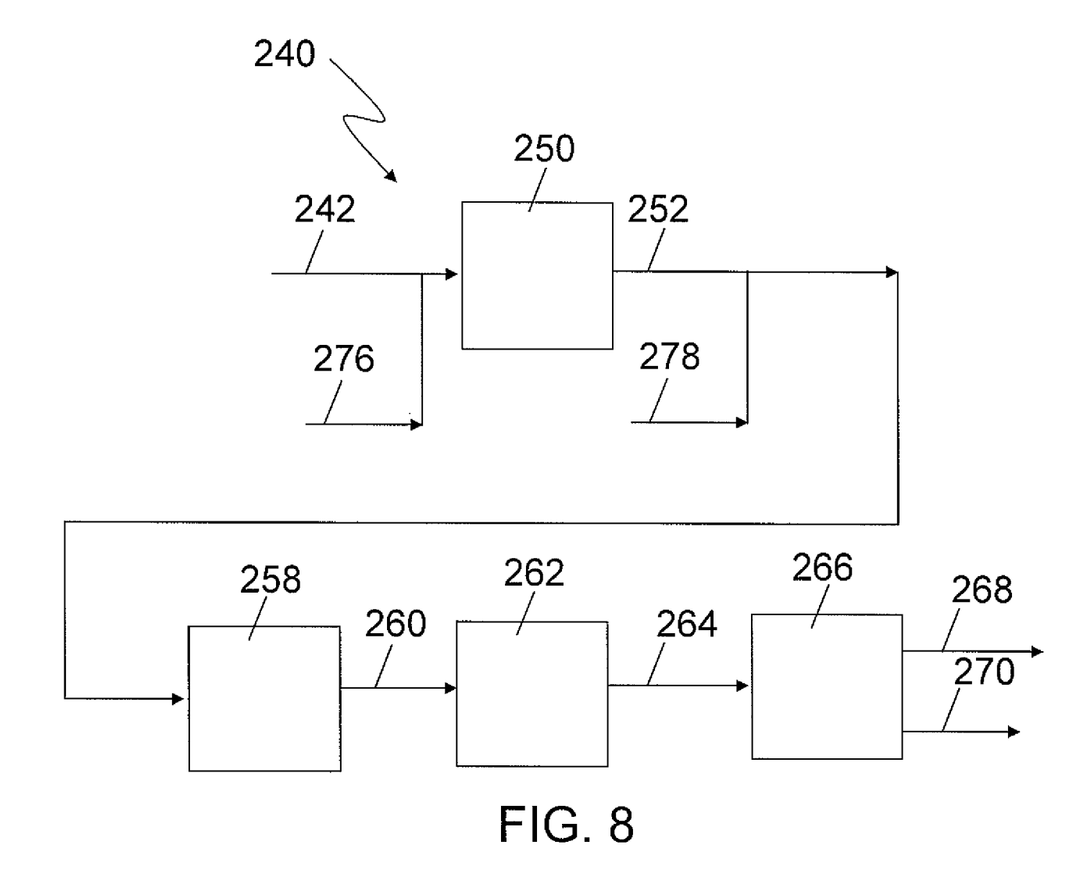
FIG. 8 illustrates a biorefinery, according to one embodiment.

FIG. 8 illustrates a cellulosic biorefinery 240, according to one embodiment. The cellulosic biorefinery 240 uses direct addition of lignin binding material 12 (not shown) and includes a feedstock stream 242 connected to a pretreatment unit 250 to form a pretreated stream 252. The pretreated stream 252 connects to a hydrolysis unit 258 to form a renewable-based feedstock stream 260. The renewable-based feedstock stream 260 connects to a conversion unit 262 to form a conversion unit effluent stream 264. The conversion unit effluent stream 264 connects to a separation unit 266 to form a product stream 268 and a byproduct stream 270. The lignin binding material 12 (not shown) can be added and/or injected at any suitable location, such as by use of a before pretreatment addition 276 and/or an after pretreatment addition 278.

Renewable material broadly refers to a substance and/or an item that has been at least partially derived from a source and/or a process capable of being replaced at least in part by natural ecological cycles and/or resources. Renewable materials may broadly include chemicals, chemical intermediates, solvents, monomers, oligomers, polymers, biofuels, biofuel intermediates, biogasoline, biogasoline blendstocks, biodiesel, green diesel, renewable diesel, biodiesel blend stocks, biodistillates, and/or the like. Desirably, but not necessarily, the renewable material may be derived from a living organism, such as plants, algae, bacteria, fungi, and/or the like.

Biofuel broadly refers to components and/or streams suitable for use as a fuel and/or a combustion source derived from renewable sources, such as may be sustainably produced and/or have reduced or no net carbon emissions to the atmosphere over an entire life cycle. Renewable resources may exclude materials mined and/or drilled, such as from the underground. Desirably, renewable resources may include single cell organisms, multicell organisms, plants, fungi, bacteria, algae, cultivated crops, non-cultivated crops, timber, materials produced by, made by or derived from any of the above organisms, and/or the like.

Biogasoline broadly refers to components and/or streams suitable for direct use and/or blending into a gasoline pool and/or octane supply derived from renewable sources, such as methane, hydrogen, syn (synthesis) gas, methanol, ethanol, propanol, butanol, dimethyl ether, methyl tert-buyl ether, ethyl tert-butyl ether, hexanol, aliphatic compounds (straight, branched, and/or cyclic), heptane, isooctane, cyclopentane, aromatic compounds, ethyl benzene, and/or the like. Butanol broadly refers to products and derivatives of 1-butanol, 2-butanol, iso-butanol, other isomers, and/or the like. Biogasoline may be used in spark ignition engines, such as automobile gasoline internal combustion engines. According to one embodiment, the biogasoline and/or biogasoline blends meet or comply with industrially accepted fuel standards.

Biodiesel broadly refers to components and/or streams suitable for direct use and/or blending into a diesel pool and/or cetane supply derived from renewable sources, such as fatty acid esters, triglycerides, lipids, fatty alcohols, alkanes, naphthas, distillate range materials, paraffinic materials, aromatic materials, aliphatic compounds (straight, branched, and/or cyclic), and/or the like. Biodiesel may be used in compression engines, such as automotive diesel internal combustion engines. In the alternative, the biodiesel may also be used in gas turbines, heaters, boilers, and/or the like. According to one embodiment, the biodiesel and/or biodiesel blends meet or comply with industrially accepted fuel standards.

Biodistillate broadly refers to components and/or streams suitable for direct use and/or blending into aviation fuels (jet), lubricating oil base stocks, kerosene fuels, and/or the like derived from renewable sources, and having a boiling point range of between about 100 degrees Celsius and about 700 degrees Celsius, between about 150 degrees Celsius and about 350 degrees Celsius, and/or the like.

According to one embodiment, the invention may include a lignin sorbent suitable for use in production of renewable materials. The sorbent may include a substrate, and a lignin binding material dispersed with respect to the substrate.

Sorbent broadly refers to a substance that can take up and hold an atom and/or a molecule, such as by absorption, adsorption, chemisorption, physisorption, ion exchange, and/or the like.

Absorption broadly refers to a physical process and/or a chemical process in which atoms, molecules, and/or ions enter a bulk phase, such as into a gas, a liquid, a solid material, and/or the like.

Adsorption broadly refers to a process that occurs when a gas solute and/or a liquid solute accumulates on a surface of a solid adsorbent and/or a liquid adsorbent, such as to form a film of molecules and/or atoms as an adsorbate, and/or the like.

Chemisorption broadly refers to a classification of adsorption characterized by a strong interaction between an adsorbate and a surface, and/or the like.

Physisorption broadly refers to a classification of adsorption characterized by a weak Van der Waals force between an adsorbate and a surface, and/or the like.

Ion exchange broadly refers to is an exchange and/or replacement of ions between two electrolytes, between an electrolyte solution and a complex and/or a molecule, and/or the like.

Substrate broadly refers to an underlying support and/or foundation, such as a substance with a permanent subject of qualities and/or the like. Desirably, the substrate for the sorbent can be at least generally inert with respect to the processes and/or environments in which it can be used. Also desirably, the substrate may include an at least generally high surface area relative to a volume of the substrate. The substrate may include any suitable material and/or composition.

Particles and/or pieces of substrate may include any suitable size and/or shape. Porous substrates may allow for a relatively larger size and/or a monolithic block shape (brick-like) for use as structured packing. In the alternative, the particles and/or pieces of substrate may include an at least generally spherical shape. The size and/or effective diameter of the substrate particle may be a function of diffusion processes and/or the like. The substrate particle may have an average effective diameter of between about 1 nanometer to about 1 micrometer, between about 1 micrometer to about 1 millimeter, between about 1 millimeter to about 1 centimeter, and/or the like, according to one embodiment.

Lignin broadly refers to a biopolymer that may be part of secondary cell walls in plants, such as a complex highly cross-linked aromatic polymer that may covalently link to hemicellulose.

Hemicellulose broadly refers to a branched sugar polymer composed mostly of pentoses, such as with a generally random amorphous structure and typically may include up to hundreds of thousands of pentose units.

Cellulose broadly refers to an organic compound with the formula $(C_6H_{10}O_5)_z$ where z includes any suitable integer. Cellulose may include a polysaccharide with a linear chain of several hundred to over ten thousand hexose units and a high degree of crystalline structure, for example.

Lytic broadly refers to and/or relates to a process and/or step of breaking down, disintegration, dissolution, lysis, and/or the like.

Enzymes broadly refer to proteins or other suitable molecules to catalyze and/or increase chemical reactions, biochemical reactions, and/or the like. Enzymes may be produced by living organisms and/or synthetic processes. Suitable enzymes may include any desirable property. Suitable enzymes may include cellulase, hemicellulase, ligninase, endo-cellulase, exo-cellulase, glucosidase, cellobiose dehydrogenase, manganese peroxidase, lignin peroxidase, and/or the like, such as to aid hydrolysis of cellulose to smaller sugar units and/or monomers.

Lignin binding material broadly refers to any suitable substance and/or material that can interact with at least a portion of lignin molecules to capture, grab, hold, and/or the like the lignin. The binding interaction may include any suitable forces, such as ionic bonding, covalent bonding, hydrogen bonding, Vander Waal forces, strong molecular forces, weak molecular forces, physical forces, mechanical forces, and/or the like.

Dispersed broadly refers to being distributed or spread widely and/or disseminated. Desirably, a state of being dispersed includes distributed at least relatively evenly on a surface of and/or impregnated throughout a medium or a material, such as the substrate. According to one embodiment, the lignin binding material may be the substrate itself, such as without other and/or additional support media.

According to one embodiment, the substrate may include alginate, agar, polyacrylamide, collagen, activated carbon, porous ceramic, diatomaceous earth, nylon, cellulose, polysulfone, polyacrylate, alumina, silica, bentonite, ion exchange resin, protein, and/or the like.

According to one embodiment, the lignin binding material may include purified proteins, mixtures of purified proteins, heterogeneous protein mixtures, distillers dried grains with solubles, whey protein, casein extract, gluten extract, cell extract, plant protein extract, and/or the like.

Protein broadly refers to complex materials and/or substances which can include amino-acid residues joined by peptide bonds. Proteins can include primarily carbon, hydrogen, nitrogen, and/or oxygen along with other elements, such as sulfur, phosphorus, iron, and/or the like. Proteins may be derived from any suitable source, such as plants, animals, and/or the like.

Distillers dried grains with solubles may also be referred to as DDGS and broadly refers to materials and/or substances remaining from production of alcohols from grains and/or cereals, such as a product obtained by condensing and drying stillage remaining after the removal of ethyl alcohol by distillation from a yeast fermentation of grain and/or grain moisture. Distillers dried grains with solubles may include a coarse fibrous material separated from a soluble and finely suspended portion, such as by use of a centrifuge. A liquid fraction can be concentrated by evaporation to a syrup which can then combined with the coarse fibrous material and dried, such as in heated air dryers. Typically, distillers dried grains with solubles can be rich in cereal, residual yeast proteins, energy, minerals, B-vitamins, growth factors, and or the like. Fermentation of starch can result in a three fold concentration of nonstarches, such as proteins, fats, minerals and vitamins. In addition to protein, vitamins and/or other growth factors can be synthesized by growing yeast cells during fermentation and can be included in the dry residue.

The lignin binding material may include any suitable lignin binding efficiency on a molar basis and/or other suitable basis. Lignin binding efficiency broadly refers to an amount of lignin captured and/or retained by the lignin binding material, such as when the lignin contacts the lignin binding material. According to one embodiment, the lignin binding material has a binding efficiency of at least about 60 percent on a molar basis, at least about 70 percent on a molar basis, at least about 80 percent on a molar basis, at least about 90 percent on a molar basis, at least about 95 percent on a molar basis, and/or the like.

The lignin binding material reversibly sorbs lignin and/or irreversibly sorbs lignin, according to one embodiment. For reversible processes, the lignin may be released upon application of a suitable agent and/or action, such as upon application of a pH change, a temperature change, a buffer solution change, a solvent polarity change, and/or the like. A pH change may include going from neutral conditions to acidic conditions and/or basic conditions with a pH adjusting agent (acid or base), for example. A temperature change may include raising the temperature by about 10 degrees Celsius, for example. A buffer solution change may include adding a different salt to the solution, for example. A solvent polarity change may include changing from an aqueous solution to an alcohol solution, for example.

According to one embodiment, the act or step of reversibly sorbing the lignin results in yields of at least about 70 percent of the bound lignin, at least about 80 percent of the bound lignin, at least about 90 percent of the bound lignin, at least about 95 percent of the bound lignin, and/or the like. Some loss and/or degradation of the lignin may occur.

The invention may include a renewable material made with and/or by any of the sorbents described herein, according to one embodiment.

According to one embodiment, the invention can include a lignin removal unit suitable for use in production of renewable materials. The unit can include a feed line for receiving a feed stream comprising soluble lignin or insoluble lignin, and at least one lignin removal device comprising a lignin sorbent for sorbing the lignin with the at least one lignin removal device in fluid communication with the feed line. The unit can also include a regeneration line for supplying a release material to the at least one lignin removal device with the regeneration line in fluid communication with the at least one lignin removal device, and a lignin line for removing the lignin from the at least one lignin removal device with the lignin line in fluid communication with the lignin removal device.

Unit broadly refers to one or more pieces of equipment and/or devices used in a process or a task. The lignin recovery unit can remove and/or recover lignin from a stream, for example.

Line broadly refers to a device for connecting and/or transmitting a substance and/or a material, such as a pipe, a channel, a conduit, a path, and/or the like. The feed line can provide an inlet into the unit with the lignin to be removed, for example. The regeneration line can provide a release material to allow the lignin to be loosed, for example. The lignin line can provide an outlet from the unit for the lignin, for example. A product line can provide an outlet from the unit for cellulose, hemicellulose, fermentable sugars, and/or the like, for example.

Stream broadly refers to a flow or a passage of a material or a substance.

Soluble lignin broadly refers to lignin at least generally susceptible to being at least partially dissolved, such as in acidic solutions, neutral solutions, alkaline solutions, buffered solutions, and/or the like.

Insoluble lignin broadly refers to lignin at least generally not susceptible to being at least partially dissolved in a solution. Insoluble lignin may include a solid particle, a suspended particle, chemically bonded to other structures (hemicellulose), and/or the like.

Lignin removal device broadly refers to any suitable process equipment and/or device for capturing the lignin from the stream. The lignin removal device may include a sorbent material, such as a packed bed, a packed column, a fluidized bed, and/or the like. The lignin removal device may include multiple vessels, such as one or more in sorption (on-line) mode, one or more in stand by (ready) mode, one or more in regeneration mode (off-line), and/or the like.

According to one embodiment, the at least one lignin removal device may include two or more packed beds each operable in sorption mode and regeneration mode. The packed beds may use any suitable arrangement of flow, such as up-flow sorption and up-flow regeneration, up-flow sorption and downflow regeneration, down-flow sorption and down-flow regeneration, and/or the like.

The sorbent used in the at least one lignin removal device may include any suitable materials. According to one embodiment, the lignin sorbent may include at least one lignin binding material such as purified proteins, mixtures of purified proteins, heterogeneous protein mixtures, distillers dried grains with solubles, whey protein, casein extract, gluten extract, cell extract, plant protein extract, and/or the like. The lignin sorbent may also include a substrate for supporting the lignin binding material where the substrate includes alginate, agar, polyacrylamide, collagen, activated carbon, porous ceramic, diatomaceous earth, nylon, cellulose, polysulfone, polyacrylate, alumina, silica, bentonite, ion exchange resin, protein, and/or the like.

The release material flowing in the regeneration line can provide any suitable material and/or action, such as a pH change, a temperature change, a buffer solution change, a solvent polarity change, washing affect, and/or the like. The temperature change can occurs through any suitable way, such as an internal heat transfer mechanism, an external heat transfer mechanism, and/or the like. Internal heat transfer may include injection of steam and/or hot water, for example. External heat transfer may include indirect heat exchange, such as with a shell and tube heat exchanger along with a suitable heat transfer media and/or stream, for example. The washing effect may include a suitable volume or quantity of material to carry away at least a portion of the lignin.

The feed stream may include any suitable material and/or substance, such as a lignocellulosic material and/or the like. The lignocellulosic material may include any suitable amount of cellulose, hemicellulose, lignin, and/or the like. The feed stream may also include a lignocellulosic hydrolyzate material, such as with carbohydrates, sugar monomers, sugar dimers, sugar trimers, sugar oligomers, and/or the like, according to one embodiment.

The invention may include a renewable material made with and/or by any of the lignin removal units described herein, according to one embodiment.

According to one embodiment, the invention may include a lignocellulosic biorefinery suitable for production of renewable materials. The biorefinery may include a pretreatment unit for depolymerization and/or solubilization of lignin, cellulose, hemicellulose and/or the like of a feedstock stream to form and/or make a pretreated stream. The biorefinery may also include at least one lignin removal unit before the pretreatment unit and/or after the pretreatment unit for removing lignin, and a hydrolysis unit for depolymerization of lignin, cellulose, hemicellulose, and/or the like to make and/or form a renewable-based feedstock steam. The biorefinery may also include a conversion unit for receiving the renewable-based feedstock stream and converting the renewable-based feedstock into a conversion unit effluent stream, and a separation unit for receiving a conversion unit effluent stream and forming and/or making a renewable material containing stream and a byproduct stream. The biorefinery also includes a regeneration line to supply release material for release of the lignin from the lignin removal unit, and a lignin line from the lignin removal unit to flow, carry, and/or remove the lignin.

Biorefinery broadly refers to a plant, an industrial complex, a collection of process units, and/or the like, such as used to produce a renewable material.

Lignocellulosic broadly refers to containing cellulose, hemicellulose, lignin, and/or the like, such as may be derived from plant material and/or the like. Lignocellulosic material may include any suitable material, such as sugar cane, sugar cane bagasse, energy cane bagasse, rice, rice straw, corn, corn stover, wheat, wheat straw, maize, maize stover, sorghum, sorghum stover, sweet sorghum, sweet sorghum stover, cotton remnant, sugar beet, sugar beet pulp, soybean, rapeseed, jatropha, switchgrass, miscanthus, other grasses, timber, softwood, hardwood, wood waste, sawdust, paper, paper waste, agricultural waste, municipal waste, any other suitable biomass material, and/or the like.

The units and/or lines of the biorefinery may include any and/or all of the characteristics and/or features described above.

The pretreatment unit may include any suitable pretreatment processes and/or equipment for chemical, thermal, and/or mechanical systems, such as steam contacting (temperature), acid contacting, base contacting, pulverizing, shredding, and/or the like. The pretreatment can disrupt a heteropolymer matrix of and/or between cellulose, hemicellulose, lignin, and/or the like. The pretreatment can render and/or make at least a portion of lignin sorbable and/or bindable, such as by a lignin sorbent and/or a lignin binding material. The pretreatment may at least partially depolymerize a portion of the cellulose and/or hemicellulose. Desirably, the pretreatment unit receives the feedstock and at least partially prepares the feedstock for subsequent units and/or processes. The pretreatment unit may include a vessel, a reactor, a tank, a basin, an agitator, an auger, a screw conveyer, a belt conveyer, a diffuser, a steam gun, a defibrator, a shredder, a grinder, a mill, a pulverizer, an aerator, a bubbler and/or the like.

The hydrolysis unit may include any suitable step, equipment, and/or process for depolymerizing of lignin, cellulose, hemicellulose and/or the like to a renewable-based feedstock by use of lytic enzymes. Desirably, the renewable-based feedstock may include six-carbon sugars (hexoses, such as glucose), five-carbon sugars (pentoses, such as xylose), and/or other materials that can be converted and/or formed into a renewable material. The hydrolysis unit may include a vessel, a reactor, a tank, a basin, an agitator, an aerator, a bubbler and/or the like. Fresh and/or new enzymes may be supplied to the hydrolysis unit.

Depolymerizing broadly refers to taking something larger and breaking it into smaller units and/or pieces. Depolymerizing may include breaking and/or severing chemical bonds, such as to release monomers (1 unit) from a polymeric backbone and/or chain. Depolymerizing may also produce dimers (2 units), trimers (3 units), tetramers (4 units), any other suitable oligomers (few units), and/or the like, such as intermediate products and/or complete products.

The conversion unit may include any suitable step, equipment, and/or process for receiving at least a portion of the renewable-based feedstock and converting the renewable-based feedstock into a renewable material. According to one embodiment, the conversion unit utilizes fermentation processes, cell culture processes and/or the like.

Fermentation broadly refers to the metabolism of carbohydrates whereby the final electron donor is not oxygen, such as anaerobically. Fermentation may include an enzyme controlled anaerobic breakdown of an energy-rich compound, such as a carbohydrate to carbon dioxide and an alcohol and/or an organic acid. In the alternative, fermentation broadly refers to biologically controlled transformation of an organic compound. Fermentation processes may use any suitable organisms, such as bacteria, fungi, algae, and/or the like. Suitable fermentation processes may include naturally occurring organisms and/or genetically modified organisms.

Cell culturing broadly refers to the metabolism of carbohydrates whereby the final electron donor is oxygen, such as aerobically. Cell culturing processes may use any suitable organisms, such as bacteria, fungi, algae, and/or the like. Suitable cell culturing processes may include naturally occurring organisms and/or genetically modified organisms.

The separation unit may include any suitable step, equipment, and/or process for receiving a conversion unit effluent stream and forming a renewable material containing stream and a byproduct stream. The separation unit may include one or more distillation columns, packed beds, mechanical devices, centrifuges, and/or the like. The byproduct stream may include yeast and/or bacteria cells from the conversion unit, for example.

According to one embodiment, the cells and/or other protein sources from the conversion unit effluent stream separated in the separation unit may at least in part be added to the either the feedstock stream and/or the pretreated stream, such as to bind lignin and/or allow more effective use of lytic enzymes in the hydrolysis unit.

The biorefinery may use any suitable amount of lytic enzymes, such as less than about 95 percent of an amount of lytic enzymes consumed in a biorefinery without a lignin removal unit, less than about 85 percent of an amount of lytic enzymes consumed in a biorefinery without a lignin removal unit, less than about 75 percent of an amount of lytic enzymes consumed in a biorefinery without a lignin removal unit, less than about 65 percent of an amount of lytic enzymes consumed in a biorefinery without a lignin removal unit, less than about 55 percent of an amount of lytic enzymes consumed in a biorefinery without a lignin removal unit, and/or the like.

According to one embodiment, the at least one lignin removal unit may include a feedstock lignin removal unit and/or a pretreated lignin removal unit. The feedstock lignin removal unit and the pretreated lignin removal unit may share or combine common pieces of equipment and/or processes. The feedstock lignin removal unit may remove lignin from the feedstock stream, such as may include a lignocellulosic material. The pretreated lignin removal unit may remove lignin from the pretreated stream, such as may include a partially depolymerized lignocellulosic material.

According to one embodiment, the biorefinery uses a lignocellulosic feedstock to produce ethanol, butanol, free fatty acids, triacylglycerides, alkyl esters, isoprenoids, lactic acid, acetic acid, butyric acid, propionic acid, any other suitable compound, and/or the like.

The invention may include a renewable material made with and/or by any of the biorefineries described herein, according to one embodiment.

According to one embodiment, the invention may include removing lignin with a process suitable for production of renewable materials. The process may include the step of sorbing lignin on a lignin sorbent to separate lignin from a remainder of an input stream, and the step of releasing the lignin from the lignin sorbent.

The step of releasing the lignin may occur by any suitable step and/or action, such as by a pH change, a temperature change, a buffer solution change, a solvent polarity change, oxidative combustion, and/or the like.

The step of sorbing may occur before and/or after a pretreatment of a lignocellulosic material (pretreating step). The pretreating step may include any suitable action and/or process, such as in aqueous solution and/or in solvent solution. Aqueous solution may include at acidic conditions (pH less than about 7.0), neutral conditions (pH equals about 7.0), alkaline conditions (pH greater than about 7.0), and/or the like. Solvent solution may include a suitable solvent, such as alcohols, ethers, esters, aldehydes, ammonia, ammonium hydroxide, ionic liquids, and/or the like.

The invention may include a renewable material made with and/or by any of the lignin removal processes described herein, according to one embodiment.

According to one embodiment, the invention may include binding lignin with a process suitable for production of renewable materials. The process may include the step of adding a lignin binding material to an input stream, and the step of converting the input stream into a renewable material. The process may include adding an exogenous and/or external source of lignin binding material to the process. In the alternative, at least a portion of the lignin binding material may be derived from the process, such as from a byproduct within a conversion effluent (yeast cells, for example). Desirably, but not necessarily, the lignin binding material includes a protein, a protein derivative, an enzyme, an enzyme derivative, and/or the like.

The lignin binding material may include any suitable material and/or compound, such as purified proteins, mixtures of purified proteins, heterogeneous protein mixtures, distillers dried grains with solubles, whey protein, casein extract, gluten extract, cell extract, plant protein extract, and/or the like. Without being bound by theory of operation, the lignin binding material can include conformations, folds, and/or other molecular structures resulting in selectivity for appropriately shaped and/or structured lignin molecules. By binding lignin, subsequent addition of lytic enzymes for hydrolysis can be more effective, such as the lignin binding material blocking and/or hindering the lytic enzymes from binding to the lignin in the feedstock. Improving the efficiency of lytic enzymes can improve an economic viability of lignocellulosic conversion to renewable materials.

The lignin binding material may be added to the process in any suitable form, such as a solid, a high-protein solid, a pellet, a granule, a solution, a slurry, a paste, a suspension, an emulsion, a dispersion, and/or the like. The lignin binding material may be injected, pumped, educted, ejected, extruded, mechanically conveyed, pneumatically conveyed, and/or the like into the process at any suitable location. The lignin binding material can be added to the process on a continuous basis, a semi-continuous basis, a discrete basis, a semi-discrete basis, a batch basis, a semi-batch basis, and/or the like.

According to one embodiment, the lignin binding material can be added to the process in a suitable amount, such as less than about 50 percent of the input stream, less than about 30 percent of the input stream, less than about 10 percent of the input stream, less than about 5 percent of the input stream, less than about 3 percent of the input stream, and/or the like on a weight basis. The lignin binding material may be added in any suitable ratio of addition of lytic enzymes, such as between about 1:100 and about 100:1, between about 10:1 and about 1:10, between about 2:1 and about 1:2, and/or the like of a mass of enzyme binding material to a mass of lytic enzymes.

Upon addition and/or mixing of the input stream and the lignin binding material, the solubilized lignin (pretreated), residual solid-phase lignin, and/or the like can be bound and/or rendered incapable of consuming and/or using lytic enzymes, such as by the lignin binding material attaching to one or more functional areas and/or sections on a lignin molecule. Multiple units and/or molecules of lignin binding material may be used with a single lignin molecule and/or unit, for example.

The input stream may include any suitable materials and/or compounds, such as cellulose, hemicellulose, lignin, soluble sugars, and/or the like.

The process may further include the step of pretreating the input stream to depolymerize and/or solubilize lignin, cellulose, hemicellulose, and/or the like. The process may further include the step of optionally cooling the input stream such as to more readily bind lignin with the lignin binding material. Cooling may include any suitable temperature, such as less than about 150 degrees Celsius, less than about 100 degrees Celsius, less than about 75 degrees Celsius, less than about 50 degrees Celsius, less than about 25 degrees Celsius, and/or the like.

The step of adding the lignin binding material may occur at any suitable step, such as before the pretreating step and/or after the pretreating step of the input stream. The pretreating may occur at any suitable condition, such as in aqueous solution at acidic conditions, neutral conditions, alkaline conditions and/or the like. In the alternative, the pretreating may occur in a solvent solution, wherein the solvent comprises alcohols, ethers, esters, aldehydes, ammonia, ammonium hydroxide, ionic liquids, and/or the like. The step of pretreating may occur at any suitable temperature, such as between about ambient temperature and about 300 degrees Celsius, between about ambient temperature and about 100 degrees Celsius, between about 100 degrees Celsius and about 250 degrees Celsius, and/or the like.

According to one embodiment, the lignin binding material can be in solution and/or a solid during pretreating, such as a soluble protein.

The lignin binding process may further include the step of adding lytic enzymes to depolymerize lignin, cellulose, hemicellulose, and/or the like.

The invention may include a renewable material made with and/or by any of the lignin binding processes described herein, according to one embodiment.

The scope of the invention is not limited merely to production of renewable materials, but broadly may be applied to and/or used with other processes and/or applications.

As used herein the terms "having", "comprising", and "including" are open and inclusive expressions. Alternately, the term "consisting" is a closed and exclusive expression. Should any ambiguity exist in construing any term in the claims or the specification, the intent of the drafter is toward open and inclusive expressions.

Regarding an order, number, sequence, and/or limit of repetition for steps in a method or process, the drafter intends no implied order, number, sequence and/or limit of repetition for the steps to the scope of the invention, unless explicitly provided.

Regarding ranges, ranges are to be construed as including all points between the upper and lower values, such as to provide support for all possible ranges contained between the upper and lower values including ranges with no upper bound and/or lower bound.

It will be apparent to those skilled in the art that various modifications and variations can be made in the disclosed structures and methods without departing from the scope or spirit of the invention. Particularly, descriptions of any one embodiment can be freely combined with descriptions or other embodiments to result in combinations and/or variations of two or more elements or limitations. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A lignin sorbent for producing-renewable materials, the sorbent comprising:
   a substrate; and
   a lignin binding material dispersed with respect to the substrate, wherein the lignin binding material comprises purified proteins, mixtures of purified proteins, heterogeneous protein mixtures, distillers dried grains with solubles, whey protein, casein extract, gluten extract, cell extract, plant protein extract, or any combination thereof;
   wherein the lignin sorbent sorbs lignin.

2. The sorbent of claim 1, wherein the substrate comprises alginate, agar, polyacrylamide, collagen, activated carbon, porous ceramic, diatomaceous earth, nylon, cellulose, polysulfone, polyacrylate, alumina, silica, bentonite, ion exchange resin, or any combination thereof.

3. The sorbent of claim 1, wherein the lignin binding material reversibly sorbs lignin.

4. The sorbent of claim 1, wherein the lignin binding material releases the lignin upon application of a pH change, a temperature change, a buffer solution change, a solvent polarity change, or any combination thereof.

5. The sorbent of claim 1, wherein the lignin binding material irreversibly sorbs lignin.

6. A lignin removal unit for producing renewable materials, the it comprising:
   a feed line for receiving a feed stream comprising soluble lignin or insoluble lignin;
   at least one lignin removal device comprising a lignin sorbent that sorbs the lignin, the at least one lignin removal device in fluid communication with the feed line;
   wherein the lignin sorbent comprises a lignin binding material comprising purified proteins, mixtures of purified proteins, heterogeneous protein mixtures, distillers dried grains with solubles, whey protein, casein extract, gluten extract, cell extract, plant protein extract, or any combination thereof; and a substrate for supporting the lignin binding material, the substrate comprising alginate, agar, polyacrylamide, collagen, activated carbon, porous ceramic, diatomaceous earth, nylon, cellulose, polysulfone, polyacrylate, alumina, silica, bentonite, ion exchange resin, or any combination thereof;
   a regeneration line for supplying a release material to the at least one lignin removal device, the regeneration line in fluid communication with the at least one lignin removal device; and
   a lignin line for removing the lignin from the at least one lignin removal device, the lignin line in fluid communication with the lignin removal device.

7. The unit of claim 6, wherein the at least one lignin removal device comprises two or more packed beds each operable in sorption mode and regeneration mode.

8. The unit of claim 6, wherein the release material provides a pH change, a temperature change, a buffer solution change, a solvent polarity change, or any combination thereof.

9. The unit of claim 6, wherein the temperature change occurs through are internal heat transfer mechanism or an external heat transfer mechanism.

10. The unit of claim 6, wherein the feed stream comprises a lignocellulosic material, the lignocellulosic material comprises cellulose, hemicellulose, lignin, or any combination thereof.

11. Removing lignin from feedstock in a process suitable for production of renewable materials, the process comprising:

sorbing lignin from the feedstock on a lignin sorbent utilizing purified proteins, mixtures of purified proteins, heterogeneous protein mixtures, distillers dried grains with solubles, whey protein, casein extract, gluten extract, cell extract, plant protein extract, or any combination thereof to separate lignin from a remainder of an input stream;

releasing the lignin from the lignin sorbent; and producing a renewable material from the feedstock having a reduced lignin content.

12. The process of claim 11, wherein the step of releasing the lignin occurs by a pH change, a temperature change, a buffer solution change, a solvent polarity change, oxidative combustion, or any combination thereof.

13. The process of claim 11, wherein the step of sorbing occurs before or after a pretreatment of a lignocellulosic material.

14. The process of claim 13, wherein the pretreatment occurs in aqueous solution at acidic, neutral, or alkaline conditions.

15. The process of claim 13, wherein the pretreatment occurs in solvent solution, and wherein the solvent comprises alcohols, ethers, esters, aldehydes, ammonia, ammonium hydroxide, ionic liquids, or any combination thereof.

* * * * *